United States Patent [19]

Nickias et al.

[11] Patent Number: 6,040,401
[45] Date of Patent: *Mar. 21, 2000

[54] SATURATED TRICYCLIC LIGAND CONTAINING METAL COMPLEXES AND OLEFIN POLYMERIZATION PROCESS

[75] Inventors: Peter N. Nickias, Midland, Mich.; Tobin J. Marks, Evanston, Ill.; Yasushi Obora, Ibaraki, Japan

[73] Assignees: The Dow Chemical Company, Midland, Mich.; Northwestern University, Evanston, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/904,363

[22] Filed: Aug. 1, 1997

Related U.S. Application Data

[60] Provisional application No. 60/023,608, Aug. 9, 1996.

[51] Int. Cl.[7] ...................................................... C08F 4/44
[52] U.S. Cl. ........................... 526/160; 526/127; 526/351; 526/943; 502/103; 502/117; 556/11; 556/53
[58] Field of Search ........................ 556/53, 11; 502/103, 502/117; 526/160, 127, 351, 943

[56] References Cited

U.S. PATENT DOCUMENTS

| 5,384,298 | 1/1995 | Inahara et al. | 502/104 |
|---|---|---|---|
| 5,385,877 | 1/1995 | Fujita et al. | 502/103 |
| 5,416,228 | 5/1995 | Ewen et al. | 556/7 |
| 5,455,317 | 10/1995 | Marks et al. | 526/126 |

FOREIGN PATENT DOCUMENTS

| 0500944 | 9/1992 | European Pat. Off. . |
|---|---|---|
| 0537130 | 4/1993 | European Pat. Off. . |
| WO 91/12285 | 8/1991 | WIPO . |

OTHER PUBLICATIONS

Giardello, et al., Chiral organolanthanides designed for asymmetric catalysis, *J. Am. Chem. Soc.* 1994, 116, 10212–10240.

*Primary Examiner*—David W. Wu
*Assistant Examiner*—Roberto Rabago

[57] ABSTRACT

Bridged, group 4 Metal complexes useful as olefin polymerization catalyst components corresponding to the formula: $L_1ZL_2MX_mX'_n$
or a dimer, solvated adduct, chelated derivative or mixture thereof, wherein:

$L_1$ is a partially saturated tricyclic group, especially octahydrofluorenyl, $L_2$ is a substituted cyclopentadienyl group that is bound to M by means of delocalized π-electrons, said cyclopentadienyl group being substituted at one and only one of its two distal positions with a bulky ligand group, Z is divalent bridging substituent, X each occurrence is a monovalent, anionic moiety having up to 40 non-hydrogen atoms, optionally, two X groups may be covalently bound together forming a divalent dianionic moiety having both valences bound to M, or, optionally 2 X groups may be covalently bound together to form a neutral, conjugated or non-conjugated diene that is bonded to M by means of delocalized π-electrons (whereupon M is in the +2 oxidation state), or further optionally one or more X and one or more X' groups may be bonded together thereby forming a moiety that is both covalently bound to M and coordinated thereto;

m is 1 or 2 and is equal to two less than the formal oxidation state of M, except when 2 X groups together form a neutral conjugated or non-conjugated diene that is π-bonded to M, in which case m is equal to the formal oxidation state of M;

X' is a neutral ligand having up to 20 non-hydrogen atoms, and n is a number from 0 to 3.

11 Claims, No Drawings

SATURATED TRICYCLIC LIGAND CONTAINING METAL COMPLEXES AND OLEFIN POLYMERIZATION PROCESS

CROSS REFERENCE STATEMENT

This application claims the benefit of U.S. provisional application No. 60/023,608, filed Aug. 9, 1996.

BACKGROUND OF THE INVENTION

This invention relates to metal complexes and to addition polymerization catalysts formed therefrom that have improved catalytic performance. More particularly the present invention relates to an addition polymerization catalyst composition comprising a Group 4 metal complex containing a saturated tricyclic ligand group. In addition, the present invention relates to catalyst compositions comprising the foregoing complexes. Finally, the invention relates to a method of using the foregoing catalyst compositions in an addition polymerization process for polymerizing addition polymerizable monomers.

In U.S. Pat. No. 5,455,317 and U.S. Pat. No. 5,416,228 there are disclosed certain bis-cyclopentadienyl metal complexes in which one cyclopentadienyl ligand contains a bulky group in one and only one distal position. The cyclopentadienyl ligand groups are desirably sterically different. The references further disclose complexes wherein the remaining cyclopentadienyl group has bilateral or pseudobilateral symmetry. Such metal complexes are useful in combination with activating cocatalysts as olefin polymerization catalysts, especially in the preparation of polymers of $C_3$ and higher α-olefins that are highly isotactic. For the teachings contained therein, the foregoing United States patents and applications are herein incorporated by reference.

It would be desirable if there were provided improved metal complexes and improved catalyst compositions derived therefrom as well as an improved addition polymerization process utilizing such catalyst compositions.

SUMMARY OF THE INVENTION

As a result of investigations carried out by the present inventors there have now been discovered new and improved Group 4 metal complexes corresponding to the formula:

$$L_1ZL_2MX_mX'_n$$

or dimers, solvated adducts, chelated derivatives or mixtures of the foregoing, wherein:

M independently each occurrence is a metal of Group 4 of the Periodic Table of the Elements;

$L_1$ is a partially saturated tricyclic group that is bound to M by means of delocalized π-electrons, said group containing up to 50 nonhydrogen atoms and corresponding to the formula:

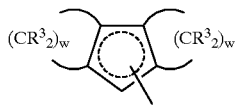

wherein $R^3$ independently each occurrence is hydrogen, or a silyl, hydrocarbyl or silyl-substituted hydrocarbyl group of up to 10 nonhydrogen atoms, and each w, independently, is a whole number from 4 to 6.

$L_2$ is a substituted cyclopentadienyl group that is bound to M by means of delocalized π-electrons, said cyclopentadienyl group being substituted at one and only one of its two distal positions with a bulky ligand group, $R^4$, said $L_2$ group containing up to 50 nonhydrogen atoms;

Z is a divalent substituent of up to 50 non-hydrogen atoms having the formula, $-(ER^2_2)_m-$, wherein E independently each occurrence is carbon, silicon or germanium, $R^2$ independently each occurrence is selected from the group consisting of hydrocarbyl, hydrocarbyloxy, silyl, and germyl of up to 20 atoms other than hydrogen, and m is an integer from 1 to 3;

X each occurrence is a monovalent, anionic moiety having up to 40 non-hydrogen atoms, optionally, two X groups may be covalently bound together forming a divalent dianionic moiety having both valences bound to M, further optionally, 2 X groups may be covalently bound together to form a neutral, conjugated or non-conjugated diene that is bonded to M by means of delocalized π-electrons (whereupon M is in the +2 oxidation state), or still further optionally one or more X and one or more X' groups may be bonded together thereby forming a moiety that is both covalently bound to M and coordinated thereto;

m is 1 or 2 and is equal to two less than the formal oxidation state of M, except when 2 X groups together form a neutral conjugated or non-conjugated diene that is π-bonded to M, in which case m is equal to the formal oxidation state of M, X' is a neutral ligand having up to 20 non-hydrogen atoms other than a diene, and optionally X' and $L_1$ or X' and $L_2$ are covalently bonded together, and n is a number from 0 to 3.

Additionally according to the present invention there is provided a catalyst composition comprising the foregoing metal complex and one or more activating cocatalysts capable of rendering the metal complex catalytically active.

In a further embodiment there is provided a supported catalyst system comprising one or more of the foregoing metal complexes, one or more activating cocatalysts, and a support material.

Finally there is provided an improved method for polymerization of addition polymerizable monomers using one or more of the above catalyst compositions or catalyst systems. Such addition polymerization processes may be used to prepare polymers for use in making molded articles, films, sheets, foamed materials and in other industrial applications.

DETAILED DESCRIPTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

Preferred $L_1$ groups for use herein are substituted or unsubstituted octahydrofluorenyl complexes corresponding to the following formula:

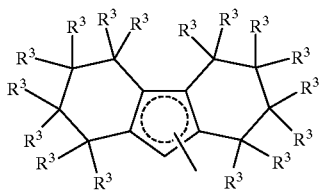

wherein R³ independently each occurrence is hydrogen or C₁₋₆ hydrocarbyl.

Highly preferred $L_1$ groups are octahydrofluorenyl and substituted octahydrofluorenyl ligands corresponding to the formula:

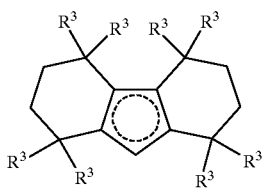

wherein R³ independently each occurrence is hydrogen or C₁₋₄ alkyl.

A most preferred $L_1$ group is octahydrofluorenyl.

Preferred $L_2$ groups are substituted cyclopentadienyl groups corresponding to the formula:

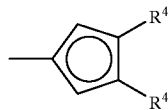

wherein one R⁴ group is hydrogen and the other R⁴ group is a C₃₋₂₀ hydrocarbyl group bonded to the cyclopentadienyl ring by means of a secondary or tertiary substituted carbon atom or an aryl group of up to 20 carbons. Most preferably one R⁴ group is hydrogen and the other R⁴ group is a cyclic hydrocarbyl group, most preferably phenyl, cyclohexyl or hydrocarbyl substituted cyclohexyl, especially menthyl.

Preferred Z groups are dimethylsilanediyl, diphenylsilanediyl, methylisopropoxysilanediyl, methylphenylsilanediyl, and 1,2-ethanediyl.

Preferred metals for use herein are titanium or zirconium, especially zirconium.

Preferred X groups herein are halide, C₁₋₂₀ hydrocarbyl, or two X groups together are a neutral C₅₋₂₀ diene, and m preferably equals 2.

Preferred X' groups include ethers, amines, and phosphines of up to 20 non-hydrogen atoms. More preferably however, n is 0.

Examples of highly preferred complexes according to the present invention correspond to the formula:

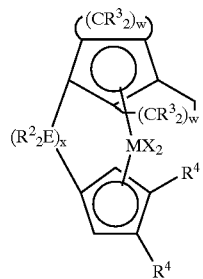

wherein:

M is titanium or zirconium in the +2, or +4 formal oxidation state;

$(R^2{}_2E)_x$ is dimethylsilane; and

X, R³ and R⁴ are as previously defined.

Specific examples include:

(octahydrofluorenyl)(3-cyclohexyl-η⁵-cyclopentadienyl) dimethylsilanezirconiumdichloride, (octahydrofluorenyl)(3-menthyl-η⁵-cyclopentadienyl) dimethylsilanezirconiumdichloride, (octahydrofluorenyl)(3-phenyl-η⁵-cyclopentadienyl) dimethylsilanezirconiumdichloride, (octahydrofluorenyl)(3-tert-butyl-η⁵-cyclopentadienyl) dimethylsilanezirconiumdichloride, (octahydrofluorenyl)(3-naphthyl-η⁵-cyclopentadienyl) dimethylsilanezirconiumdichloride, (octahydrofluorenyl)(3-cyctohexyl-η⁵-cyclopentadienyl) dimethylsilanezirconiumdimethyl, (octahydrofluorenyl)(3-menthyl-η⁵-cyclopentadienyl) dimethylsilanezirconiumdimethyl, (octahydrofluorenyl)(3-phenyl-η⁵-cyclopentadienyl) dimethylsilanezirconiumdimethyl, (octahydrofluorenyl)(3-tert-butyn-η⁵-cyclopentadienyl) dimethylsilanezirconiumdimethyl, (octahydrofluorenyl)(3-naphthyl-η⁵-cyclopentadienyl) dimethylsilanezirconiumdimethyl, (octahydrofluorenyl)(3-cyctohexyl-η⁵-cyclopentadienyl) dimethylsilanetitanium (II) (1,4-diphenylbutadiene), (octahydrofluorenyl)(3-menthyl-η⁵-cyclopentadienyl) dimethylsilanetitanium (II) (1,4-diphenylbutadiene), (octahydrofluorenyl)(3-phenyl-η⁵-cyclopentadienyl) dimethylsilanetitanium (II) (1,4-diphenylbutadiene), (octahydrofluorenyl)(3-tert-butyl-η⁵-cyclopentadienyl) dimethylsilanetitanium (II) (1,4-diphenylbutadiene), (octahydrofluorenyl)(3-naphthyl-η⁵-cyclopentadienyl) dimethylsilanetitanium (II) (1,4-diphenylbutadiene), (octahydrofluorenyl)(3-cyclohexyl-η⁵-cyclopentadienyl) dimethylsilanezirconiumdichloride, (2,2,5,5,6,6,9,9-octamethyloctahydrofluorenyl)(3-menthyl-η⁵-cyclopentadienyl) dimethylsilanezirconiumdimethyl, (2,2,5,5,6,6,9,9-octamethyloctahydrofluorenyl)(3-phenyl-η⁵-cyclopentadienyl) 1,2-ethanediyllzirconiumdibenzyl, (2,2,5,5,6,6,9,9-octamethyloctahydrofluorenyl)(3-tert-butyl-η⁵-cyclopentadienyl) dimethylsilanehafniumdichloride, and (2,2,5,5,6,6,9,9-octamethyloctahydrofluorenyl)(3-naphthyl-η⁵-cyclopentadienyl) dimethylsilanezirconiumdichloride.

The complexes are rendered catalytically active by combining them with an activating cocatalyst or by use of an activating technique. Suitable activating cocatalysts for use herein include polymeric or oligomeric alumoxanes, especially methylalumoxane, triisobutyl aluminum-modified methylalumoxane, or diisobutylalumoxane; strong Lewis acids, such as $C_{1-30}$ hydrocarbyl substituted Group 13 compounds, especially tri(hydrocarbyl)aluminum- or tri(hydrocarbyl)boron-compounds and halogenated derivatives thereof, having from 1 to 10 carbons in each hydrocarbyl or halogenated hydrocarbyl group, especially tris(pentafluorophenyl)borane; and nonpolymeric, inert, compatible, noncoordinating, ion forming compounds (including the use of such compounds under oxidizing conditions). A suitable activating technique is bulk electrolysis (explained in more detail hereinafter). Combinations of the foregoing activating cocatalysts and techniques may also be employed if desired. The foregoing activating cocatalysts and activating techniques have been previously taught with respect to different metal complexes in the following references: EP-A-277,003, U.S. Pat. No. 5,153,157, U.S. Pat. No. 5,064,802, EP-A-468,651 (equivalent to U.S. Ser. No. 07/547,718, now abandoned), EP-A-520,732 (equivalent to U.S. Ser. No. 07/876,268, now U.S. Pat. No. 5,721,185), and U.S. Pat. No. 5,350,723, teachings of which are hereby incorporated by reference.

Suitable nonpolymeric, inert, compatible, noncoordinating, ion forming compounds useful as cocatalysts in one embodiment of the present invention comprise a cation which is a Bronsted acid capable of donating a proton, and a compatible, noncoordinating, anion, $A^-$. Preferred anions are those containing a single coordination complex comprising a charge-bearing metal or metalloid core which anion is capable of balancing the charge of the active catalyst species (the metal cation) which is formed when the two components are combined. Also, said anion can be displaced by olefinic, diolefinic and acetylenically unsaturated compounds or other compounds such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are well known and many, particularly such compounds containing a single boron atom in the anion portion, are available commercially.

Preferably such cocatalysts may be represented by the following general formula:

$$(L^*-H)^+_d A^{d-}$$

wherein:
L* is the conjugate Lewis base of $L^*H^+$;
$(L^*-H)^+$ is a Bronsted acid;
$A^{d-}$ is a noncoordinating, compatible anion having a charge of d–, and d is an integer from 1 to 3.
More preferably d is one, that is, $A^{d-}$ is $A^-$.
Highly preferably, $A^-$ corresponds to the formula: 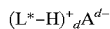
wherein:
B is boron in the +3 formal oxidation state; and
Q independently each occurrence is selected from hydride, dialkylamido, halide, alkoxide, aryloxide, hydrocarbyl, halocarbyl, and halo-substituted-hydrocarbyl radicals, said Q having up to 20 carbons with the proviso that in not more than one occurrence is Q halide.
In a more highly preferred embodiment, Q is a fluorinated $C_{1-20}$ hydrocarbyl group, most preferably, a fluorinated aryl group, especially, pentafluorophenyl.

Illustrative, but not limiting, examples of ion forming compounds comprising proton donatable cations which may be used as activating cocatalysts in the preparation of the catalysts of this invention are tri-substituted ammonium salts such as:
trimethylammonium tetraphenylborate,
methyidioctadecylammonium tetraphenylborate,
triethylammonium tetraphenylborate,
tripropylammonium tetraphenylborate,
tri(n-butyl)ammonium tetraphenylborate,
methyltetradecyloctadecylammonium tetraphenylborate,
N,N-dimethylanilinium tetraphenylborate,
N,N-diethylanilinium tetraphenylborate,
N,N-dimethyl(2,4,6-trimethylanilinium) tetraphenylborate,
trimethylammonium tetrakis(penta-fluorophenyl)borate,
triethylammonium tetrakispentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-diethylanilinium tetrakis(pentafluorophenyl)borate,
N,N-dimethyl(2,4,6-trimethylanilinium) tetrakis(pentafluorophenyl)borate,
trimethylammonium tetrakis(2,3,4,6-tetrafluorophenylborate,
triethylammonium tetrakis(2,3,4,6-tetrafluorophenyl)borate,
tripropylammonium tetrakis(2,3,4,6-tetrafluorophenyl)borate,
tri(n-butyl)ammonium tetrakis(2,3,4,6-tetrafluorophenyl)borate,
dimethyl(t-butyl)ammonium tetrakis(2,3,4,6-tetrafluorophenyl)borate,
N,N-dimethylanilinium tetrakis(2,3,4,6-tetrafluorophenyl)borate,
N,N-diethylanilinium tetrakis(2,3,4,6-tetrafluorophenyl)borate, and
N,N-dimethyl-(2,4,6-trimethylanilinium) tetrakis-(2,3,4,6-tetrafluoro- phenyl)borate.
Dialkyl ammonium salts such as:
di-(i-propyl)ammonium tetrakis(pentafluorophenyl)borate, and
dicyclohexylammonium tetrakis(pentafluorophenyl)borate.
Tri-substituted phosphonium salts such as:
triphenylphosphonium tetrakis(pentafluorophenyl)borate,
tri(o-tolyl)phosphonium tetrakis(penta-fluorophenyl)borate, and
tri(2,6-dimethylphenyl)phosphonium tetrakis(pentafluorophenyl)borate.

Preferred are tetrakis(pentafluorophenyl)borate salts of long chain alkyl mono- and disubstituted ammonium complexes, especially $C_{14}$–$C_{20}$ alkyl ammonium complexes, especially methyldi(octadecyl)ammonium tetrakis(pentafluorophenyl)borate and methyldi(tetradecyl) ammonium tetrakis(pentafluorophenyl)borate.

Another suitable ion forming, activating cocatalyst comprises a salt of a cationic oxidizing agent and a noncoordinating, compatible anion represented by the formula:

$(Ox^{e+})_d(A^{d-})_e$ wherein:

Ox$^{e+}$ is a cationic oxidizing agent having charge e+;

e is an integer from 1 to 3; and

A$^{d-}$, and d are as previously defined.

Examples of cationic oxidizing agents include: ferrocenium, hydrocarbyl-substituted ferrocenium, Ag$^+$, or Pb$^{+2}$. Preferred embodiments of A$^{d-}$ are those anions previously defined with respect to the Bronsted acid containing activating cocatalysts, especially tetrakis (pentafluorophenyl)borate.

Another suitable ion forming, activating cocatalyst comprises a compound which is a salt of a carbenium ion or silylium ion and a noncoordinating, compatible anion represented by the formula:

©$^+$A$^-$ wherein:

©$^+$ is a C$_{1-20}$ carbenium ion or silylium ion; and

A$^-$ is as previously defined.

A preferred carbenium ion is the trityl cation, that is triphenylcarbenium. A preferred silylium ion is triphenylsilylium.

The foregoing activating technique and ion forming cocatalysts are also preferably used in combination with a tris(hydrocarbyl)-aluminum compound having from 1 to 10 carbons in each hydrocarbyl group, an oligomeric or polymeric alumoxane compound, a bis(hydrocarbyl) (hydrocarbyloxy)aluminum compound having from 1 to 20 carbons in each hydrocarbyl or hydrocarbyloxy group, or a mixture of the foregoing compounds, if desired. These aluminum compounds are usefully employed for their beneficial ability to scavenge impurities such as oxygen, water, and aldehydes from the polymerization mixture.

Suitable bis(hydrocarbyl)(hydrocarbyloxy)aluminum compounds correspond to the formula T$^1{}_2$A|OT$^2$ wherein T$^1$ is C$_{3-6}$ secondary or tertiary alkyl, most preferably isopropyl, isobutyl or tert-butyl; and T$^2$ is a C$_{12-30}$ alkaryl radical or aralkyl radical, most preferably, 2,6-di(t-butyl)-4-methylphenyl, 2,6-di(t-butyl)-4-methyltolyl, 2,6-di(i-butyl)-4-methylphenyl, or 4-(3',5'-ditertiarybutyltolyl)-2,6-ditertiarybutylphenyl.

Preferred aluminum compounds include C$_{2-6}$ trialkyl aluminum compounds, especially those wherein the alkyl groups are ethyl, propyl, isopropyl, n-butyl, isobutyl, pentyl, neopentyl, or isopentyl, dialkyl(aryloxy)aluminum compounds containing from 1–6 carbons in the alkyl group and from 6 to 18 carbons in the aryl group (especially (3,5-di (t-butyl)-4-methylphenoxy)diisobutylaluminum), methylalumoxane, modified methylalumoxane and diisobutylalumoxane. The molar ratio of aluminum compound to metal complex is preferably from 1:10,000 to 1000:1, more preferably from 1:5000 to 100:1, most preferably from 1:100 to 100:1.

An especially preferred activating cocatalyst comprises the combination of a trialkyl aluminum compound having from 1 to 4 carbons in each alkyl group and an ammonium salt of tetrakis(pentafluoro-phenyl)borate, in a molar ratio from 0.1:1 to 1:0.1, optionally up to 1000 mole percent of an alkylalumoxane with respect to M, is also present.

The activating technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0 to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), DME, and mixtures thereof.

The electrolysis may be conducted in a standard electrolytic cell containing an anode and cathode (also referred to as the working electrode and counter electrode respectively). Suitably materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally, an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and an inert, compatible, noncoordinating anion, A$^-$. Preferred supporting electrolytes are salts corresponding to the formula: G$^+$A$^-$; wherein:

G$^+$ is a cation which is nonreactive towards the starting and resulting complex, and A$^-$ is a noncoordinating, compatible anion.

Examples of cations, G$^+$, include tetrahydrocarbyl substituted ammonium or phosphonium cations having up to 40 nonhydrogen atoms. A preferred cation is the tetra-n-butylammonium cation.

During activation of the complexes of the present invention by bulk electrolysis the cation of the supporting electrolyte passes to the counter electrode and A$^-$ migrates to the working electrode to become the anion of the resulting oxidized product. Either the solvent or the cation of the supporting electrolyte is reduced at the counter electrode in equal molar quantity with the amount of oxidized metal complex formed at the working electrode.

Preferred supporting electrolytes are tetrahydrocarbylammonium salts of tetrakis(perfluoroaryl) borates having from 1 to 10 carbons in each hydrocarbyl group, especially tetra-n-butylammonium tetrakis(pentafluorophenyl) borate.

The molar ratio of catalyst/cocatalyst employed preferably ranges from 1:10,000 to 100:1, more preferably from 1:5000 to 10:1, most preferably from 1:10 to 1:2.

In general, the catalysts can be prepared by combining the two components (metal complex and activator) in a suitable solvent at a temperature within the range from about −100° C. to about 300° C. or by generating the activated catalyst electrochemically as previously explained. The activated catalyst may be separately prepared prior to use by combining the respective components or prepared in situ by combination in the presence of the monomers to be polymerized. It is preferred to form the activated catalyst in situ due to the exceptionally high catalytic effectiveness of activated catalysts prepared in this manner. The catalyst and cocatalyst as well as activated catalyst are sensitive to both moisture and oxygen and should be handled and transferred in an inert atmosphere.

As previously mentioned, the present metal complexes are highly desirable for use in preparing supported catalysts. Especially suited substrates include alumina, silica and prepolymerized polymeric substrates. Suitable supported catalyst systems are readily prepared by contacting the present metal complexes with the substrate, optionally while subjecting the mixture to heating and/or reduced pressures.

Preferred supports for use in the present invention include highly porous silicas, aluminas, aluminosilicates, and mixtures thereof. The most preferred support material is silica. The support material may be in granular, agglomerated, pelletized, or any other physical form. Suitable materials include, but are not limited to, silicas available from Grace Davison (division of W.R. Grace & Co.) under the designations SD 3216.30, Davison Syloid 245, Davison 948 and Davison 952, and from Degussa AG under the designation Aerosil 812; and aluminas available from Akzo Chemicals Inc. under the designation Ketzen Grade B.

Supports suitable for the present invention preferably have a surface area as determined by nitrogen porosimetry using the B.E.T. method from 10 to about 1000 m$^2$/g, and preferably from about 100 to 600 m$^2$/g. The pore volume of the support, as determined by nitrogen adsorption, advantageously is between 0.1 and 3 cm$^3$/g, preferably from about 0.2 to 2 cm$^3$/g. The average particle size is not critical, but typically is from 0.5 to 500 μm, preferably from 1 to 100 μm.

Both silica and alumina are known to inherently possess small quantities of hydroxyl functionality attached to the crystal structure. When used as a support herein, these materials are preferably subjected to a heat treatment and/or chemical treatment to reduce the hydroxyl content thereof. Typical heat treatments are carried out at a temperature from 30 to 1000° C. for a duration of 10 minutes to 50 hours in an inert atmosphere or under reduced pressure. Typical chemical treatments include contacting with Lewis acid alkylating agents such as trihydrocarbyl aluminum compounds, trihydrocarbylchlorosilane compounds, trihydrocarbylalkoxysilane compounds or similar agents. Preferred silica or alumina materials for use herein have a surface hydroxyl content that is less than 0.8 mmol hydroxyl groups per gram of solid support, more preferably less than 0.5 mmol per gram. The hydroxyl content may be determined by adding an excess of dialkyl magnesium to a slurry of the solid support and determining the amount of dialkyl magnesium remaining in solution via known techniques. This method is based on the reaction:

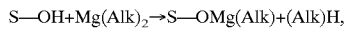

S—OH+Mg(Alk)$_2$→S—OMg(Alk)+(Alk)H, wherein S is the solid support, and Alk is a C$_{1-4}$ alkyl group.

The support may be unfunctionalized (excepting for hydroxyl groups as previously disclosed) or functionalized by treating with a silane or chlorosilane functionalizing agent to attach thereto pendant silane —(Si—R)=, or chlorosilane —(Si—Cl)= functionality, wherein R is a C$_{1-10}$ hydrocarbyl group. Suitable functionalizing agents are compounds that react with surface hydroxyl groups of the support or react with the silicon or aluminum of the matrix. Examples of suitable functionalizing agents include phenylsilane, diphenylsilane, methylphenylsilane, dimethylsilane, diethylsilane, dichlorosilane, and dichlorodimethylsilane. Techniques for forming such functionalized silica or alumina compounds were previously disclosed in U.S. Pat. Nos. 3,687,920 and 3,879,368, the teachings of which are herein incorporated by reference.

The support may also be treated with an aluminum component selected from an alumoxane or an aluminum compound of the formula AlR$_3$, wherein R independently each occurrence is hydride or R$^1$, and R$^1$ is C$_{1-4}$ alkyl. Preferably, the aluminum component is selected from the group consisting of aluminoxanes and tris(C$_{1-4}$ alkyl) aluminum compounds. Most preferred aluminum components are aluminoxanes, trimethylaluminum, triethylaluminum, tri-isobutylaluminum, and mixtures thereof.

Alumoxanes (also referred to as aluminoxanes) are oligomeric or polymeric aluminum oxy compounds containing chains of alternating aluminum and oxygen atoms, whereby the aluminum carries a substituent, preferably an alkyl group. The structure of alumoxane is believed to be represented by the following general formulae, (—Al(R$^1$)—O)$_m$', for a cyclic alumoxane, and R$^1{}_2$Al—O(—Al(R$^1$)—O)$_m$'—AlR$^1{}_2$, for a linear compound, wherein R$^1$ is C$_{1-4}$ alkyl, and m' is an integer ranging from 1 to about 50, preferably at least about 4. Alumoxanes are typically the reaction products of water and an alkylaluminum compound, which in addition to an alkyl group may contain halide or alkoxide groups. Reacting several different alkylaluminum compounds, such as for example trimethylaluminum and tri-isobutylaluminum, with water yields so-called modified or mixed alumoxanes. Preferred alumoxanes are methylalumoxane and methylalumoxane modified with minor amounts of C$_{2-4}$ alkyl groups, especially isobutyl groups. Alumoxanes generally contain minor to substantial amounts of starting alkylaluminum compound.

Particular techniques for the preparation of alumoxane type compounds by contacting an alkylaluminum compound with an inorganic salt containing water of crystallization are disclosed in U.S. Pat. No. 4,542,119. In a particular preferred embodiment an alkylaluminum compound is contacted with a regeneratable water-containing substance such as hydrated alumina, silica or other substance. This is disclosed in EP-A-338,044. Thus the alumoxane may be incorporated into the support by reaction of a hydrated alumina or silica material, which has optionally been functionalized with silane, siloxane, hydrocarbyloxysilane, or chlorosilane groups, with a tris(C$_{1-10}$ alkyl) aluminum compound according to known techniques. For the teachings contained therein the foregoing patents and publications, or there corresponding equivalent United States applications, are hereby incorporated by reference.

The treatment of the support material in order to also include optional alumoxane or trialkylaluminum loadings involves contacting the same with an alumoxane or trialkylaluminum compound before, after, or simultaneously with addition of the complex or activated catalyst. Optionally the mixture can also be heated under an inert atmosphere for a period and at a temperature sufficient to fix the alumoxane, trialkylaluminum compound, complex or catalyst system to the support. Optionally, the treated support component containing alumoxane or the trialkylaluminum compound may be subjected to one or more wash steps, using toluene or similar solvent, to remove excess alumoxane or trialkylaluminum that is not fixed to the support.

Besides contacting the support with alumoxane, the alumoxane may be generated in situ by contacting an unhydrolyzed silica or alumina or a moistened silica or alumina with a trialkyl aluminum compound optionally in the presence of an inert diluent. Such a process is well known in the art, having been disclosed in EP-A-250,600, U.S. Pat. No. 4,912,075, and U.S. Pat. No. 5,008,228, the teachings of which, or of the corresponding U.S. application, are hereby incorporated by reference. Suitable aliphatic hydrocarbon diluents include pentane, isopentane, hexane, heptane, octane, isooctane, nonane, isononane, decane, cyclohexane, methylcyclohexane and combinations of two or more of such diluents. Suitable aromatic hydrocarbon diluents are benzene, toluene, xylene, and other alkyl or halogen substituted aromatic compounds. Most preferably, the diluent is an aromatic hydrocarbon, especially toluene. After preparation in the foregoing manner the residual hydroxyl content thereof is desirably reduced to a level less than 1.0 meq of OH per gram of support, by any of the previously disclosed techniques.

The catalysts, whether or not supported in any of the foregoing methods, may be used to polymerize ethylenically and/or acetylenically unsaturated monomers having from 2 to 100,000 carbon atoms either alone or in combination. Preferred monomers include the $C_{2-20}$ α-olefins especially ethylene, propylene, isobutylene, 1-butene, 1-pentene, 1-hexene, 3-methyl-1-pentene, 4-methyl-1-pentene, 1-octene, 1-decene, long chain macromolecular α-olefins, and mixtures thereof. Other preferred monomers include styrene, $C_{1-4}$ alkyl substituted styrene, tetrafluoroethylene, vinylbenzocyclobutane, ethylidenenorbornene, 1,4-hexadiene, 1,7-octadiene, vinylcyclohexane, 4-vinylcyclohexene, divinylbenzene, and mixtures thereof with ethylene. Long chain macromolecular α-olefins are vinyl terminated polymeric remnants formed in situ during continuous solution polymerization reactions. Under suitable processing conditions such long chain macromolecular units are readily polymerized into the polymer product along with ethylene and other short chain olefin monomers to give small quantities of long chain branching in the resulting polymer. Most preferably the present metal complexes are used in the polymerization of propylene to prepare polypropylene having a high degree of isotacticity.

In general, the polymerization may be accomplished at conditions well known in the prior art for Ziegler-Natta or Kaminsky-Sinn type polymerization reactions, such as temperatures from 0–250° C. and pressures from atmospheric to 1000 atmospheres (0.1 to 100 MPa). Suspension, solution, slurry, gas phase or other process conditions may be employed if desired. The support, if present, is preferably employed in an amount to provide a weight ratio of catalyst (based on metal):support from 1:100,000 to 1:10, more preferably from 1:50,000 to 1:20, and most preferably from 1:10,000 to 1:30. Suitable gas phase reactions may utilize condensation of the monomer or monomers employed in the reaction, or of an inert diluent to remove heat from the reactor.

In most polymerization reactions the molar ratio of catalyst:polymerizable compounds employed is from $10^{-12}:1$ to $10^{-1}:1$, more preferably from $10^{-12}:1$ to $10^{-5:1}$.

Suitable solvents for polymerization via a solution process are noncoordinating, inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and aromatic and alkyl-substituted aromatic compounds such as benzene, toluene, and xylene. Suitable solvents also include liquid olefins which may act as monomers or comonomers including ethylene, propylene, 1-butene, butadiene, cyclopentene, 1-hexene, 3-methyl-1-pentene, 4-methyl-1-pentene, 1,4-hexadiene, 1,7-octadiene, 1-octene, 1-decene, styrene, divinylbenzene, ethylidenenorbornene, allylbenzene, vinyltoluene (including all isomers alone or in admixture), 4-vinylcyclohexene, and vinylcyclohexane. Mixtures of the foregoing are also suitable.

The catalysts may also be utilized in combination with at least one additional homogeneous or heterogeneous polymerization catalyst in the same or in separate reactors connected in series or in parallel to prepare polymer blends having desirable properties. An example of such a process is disclosed in WO 94/00500, equivalent to U.S. Ser. No. 07/904,770, now abandoned, as well as U.S. Ser. No. 08/10958, filed Jan. 29, 1993, now abandoned, the teachings or which are hereby incorporated by reference herein.

One such polymerization process comprises: contacting, optionally in a solvent, one or more α-olefins with a catalyst according to the present invention, in one or more continuous stirred tank or tubular reactors, connected in series or parallel, or in the absence of solvent, optionally in a fluidized bed gas phase reactor, and recovering the resulting polymer. Condensed monomer or solvent may be added to the gas phase reactor as is well known in the art.

The skilled artisan will appreciate that the invention disclosed herein may be practiced in the absence of any component which has not been specifically disclosed.

EXAMPLE 1

Preparation of (octahydrofluorenyl)(3-menthyl-$\eta^5$-cyclopentadienyl) dimethylsilylzirconiumdichloride
($OHF-Me_2Si-MCp)ZrCl_2$ All manipulations of air-sensitive materials were performed with rigorous exclusion of oxygen and moisture in flamed Schlenk-type glassware on a dual manifold Schlenk line or interfaced to a high-vacuum ($10^{-6}$ Torr) line or in a nitrogen-filled Vacuum Atmospheres glovebox with a high-capacity recirculator (1–2 ppm of $O_2$). Argon (Matheson, prepurified), nitrogen(Matheson, prepurified), ethylene (Matheson, polymerization grade), and propylene (Matheson, polymerization grade) were purified by passage through a MnO/vermiculite oxygen-removal column and an activated Davison 4 Å molecular sieve column, followed by passage over MnO/silica. Ether solvents were purified by distillatation from Na/K alloy/benzophenone ketyl. Hydrocarbon solvents (toluene and pentane) were distilled under nitrogen from Na/K alloy. All solvents for vacuum line manipulations were stored in vacuo over Na/K alloy in resealable bulbs. Deuterated solvents were obtained from Cambridge Isotope Laboratories (all 99+atom percent D) and were freeze-pump-thaw degassed. Non-halogenated solvents were dried over Na/K alloy, and halogenated solvents were dried over $P_2O_5$ and stored over activated Davison 4 Å molecular sieves. $ZrCl_4$ (Aldrich 99.99 percent) was used without further purification. The chiral ligand reagent Na[(−)menthylCp]$^2$ was prepared as previously described by Giardello, et al., *J. Am. Chem. Soc.* 1994, 116, 10212–10240. $B(C_6F_5)_3$, and $Ph_3CB(C_6F_5)_4$ were prepared according to the techniques disclosed in Massey, A. G., et al.,*J. Organomet. Chem.*, 1964, 2, 245–250 and Chien, J. C.

W., et al., *J. Am. Chem. Soc.*, 1984, 106, 6355–6364. Solid methylalumoxane was obtained by slow removal of solvent in vacuo ($10^{-6}$ torr) at 25° C. from a solution of MAO (Schering, 20 wt percent solution in toluene). Prolonged evacuation (12–16 h) of the residual solids removed a majority of the $AlMe_3$.

Physical and Analytical Measurements. NMR spectra were recorded on either a Varian VXR 300 (FT, 300 MHz, $^1H$; 75 MHz, $^{13}C$), or a Varian XL-400 (FT, 400 MHz, $^1H$; 100 MHz, $^{13}C$) instrument. Chemical shifts for $^1H$ and $^{13}C$ are referenced to internal solvent resonances and are reported relative to tetramethylsilane. Neat methanol or ethylene glycol were used as temperature standards in all variable temperature NMR experiments. NMR experiments on air-sensitive samples were conducted in either Teflon valve-sealed tubes (J. Young) or in screw-capped tubes fitted with septa (Wilmad). Circular dichroism (CD) spectra were recorded on a Jasco J-500 spectrophotometer equipped with a JASCO DP-500/AT software package (version 1.2). Air-sensitive samples were prepared in 10 mm path length cylindrical quartz cuvettes (Helma Cells) fitted with Teflon needle valves. Solvent blanks were recorded under identical conditions and the baseline subtracted from the experimental spectrum. Molar ellipticities [θ] are reported relative to absorption maxima in units of degree•$cm^2$•$decimol^{-1}$. Elemental analyses were performed by Oneida Research Services, Inc., Whitesboro, N.Y.

Octahydrofluorenyl Li In a 2L flask, 500 mL of concentrated sulfuric acid was stirred with a mechanical stirrer. To this was added 1-adamantanol (68.1 g, 0.44 mol) which partially dissolved. To this mixture 40.0 g (0.22 mol) of perhydrofluorene was added dropwise and after addition was complete, the reaction mixture was stirred for 3 hours. After this time period, the acid was extracted with hexane (3×500 mL). The acid was next carefully poured into 3000 mL of ice water. The aqueous solution was then extracted with ether (3×600 mL). The combined ether extracts were washed with water (3×600 mL). The ether extract was then dried over $MgSO_4$. The ether was then removed on the rotavap leaving an orange oil. The oil was then dissolved in hexane and passed through a silica gel column eluting with hexane. The hexane was removed under reduced pressure to give a mixture of dienes (analyzed via GC) weighing 27.5 g (0.16 mol). The diene mixture was then degassed and combined with 200 mL of pentane. To this solution, 66.4 mL (0.17 mol) of n-BuLi (2.5 M solution in hexanes) was added dropwise and stirred overnight. The resulting solid was then collected via suction filtration, washed with pentane, and dried under reduced pressure to give 12.4 g (0.068 mol, 44 percent) of title compound.

(Octahydrofluorenyl)dimethylchlorosilane A 500 mL Schlenk flask with a Teflon inlet valve was charged with Li(octahydrofluorenyl) (12.5 g, 0.068 mol). Under Ar flush, THF 100 mL was syringed into the reaction flask. Dichlorodimethylsilane (30 mL, 0.218 mol) was then added dropwise over 30 min to the suspension at −78° C. Within 2 h, the white suspension solution turned to pale yellow clear solution, and the solution was stirred overnight at room temperature. After evaporation of the THF, the residue was extracted with 100 mL of ether, filtered, and the ether removed from the filtrate under reduced pressure. The pure $Me_2SiCl$(octahydrofluorenide) was obtained by fractional distillation at 80–82° C./0.04 mmHg (10.7 g, 0.040 mmol, 58 percent yield). $^{13}C$ NMR ($C_6D_6$) δ 0.52, 22.83, 22.98, 23.74, 26.57, 44.80, 53.17, 135.17, 139.53.

(Octahydrofluorenyl)(3-menthylcyclopentadienyl) dimethylsilane A 250 mL flask with a Teflon inlet was charged with Na[(−)-menthylCp (8.98 g, 0.040 mmol) in the glove box. THF (150 mL) was added via syringe to the reaction flask. The mixture was stirred, completely dissolving the solids and affording a clear, pale yellow solution. Under an argon flush, a solution of $Me_2SiCl$ (octahydrofluorenide) (10.7 g, 0.040 mol) was syringed into the stirred solution of the sodium salt. Immediate precipitation of a flocculent, colorless solid (NaCl) occurred. The suspension was stirred at ambient temperature for 18 h. The solvent was then removed under reduced pressure, and the residue extracted with 250 mL of pentane. The pentane solution was reduced to 50 mL, cooled to −78° C., and the pure compound (14.5 g, 0.035 mol, 88 percent yield) was obtained by recrystallization as a mixture of two isomers. $^1H$ NMR ($C_6D_6$) δ −0.07 (d, 3H), 0.05 (d, 3H), 0.82–2.03 (m, 36H), 2.17–2.50 (m, 12H), 2.73 (s, 1H), 3.38 (d, 1H), 6.13 (s, 1H), 6.45 (s, 1H), 6.61 (s, 1H). $^{13}C$ NMR ($C_6D_6$) δ −4.87, −4.25, −4.17, −3.71, 14.32, 15.70, 21.82, 22.75, 22.93, 23.25, 23.59, 24.40, 24.71, 24.82, 27.50, 28.03, 33.38, 34.48, 35.73, 42.98, 44.61, 44.82, 47.21, 47.54, 48.17, 48.36, 52.58, 126.95, 127.02, 130.94, 131.71, 134.00, 136.71, 136.80, 137.92, 150.59.

(Octahydrofluorenyl)(3-menthylcyclopentadienyl) dimethylsilane dilithium. A 250 mL flask with a Teflon inlet valve was charged with-(octahydrofluorenyl)(3-menthylcyclopentadienyl)dimethylsilane (2.00 g, 4.82 mmol) in the glove box. Pentane (50 mL) was added via syringe to the reaction flask. The mixture was stirred, completely dissolving the solid and affording a clear, pale yellow solution. Under an argon flush, a solution of $LiCH_2$ (TMS) (91 mg, 9.64 mmol) in pentane (30 mL) was syringed into the stirred solution. The solution was stirred at a ambient temperature for 10 h. The solvent was then removed in vacuo, and the resulting solid was used without further purification. $^1H$ NMR (THF-$d_8$): δ 0.00 (s, 3H), 0.02 (s, 3H), 0.68 (d, 4H), 0.72 (d, 4H), 0.88 (d, 4H), 0.93–1.76 (m, 15H), 1.88–2.17 (m, 6H), 2.27–2.38 (m, 1H), 2.77 (s, 1H), 5.71–5.77 (m, 2H), 5.85 (s, 1H). $^{13}C$ NMR (THF-$d_8$) δ 3.82, 3.97, 16.16, 22.39, 23.42, 25.90, 25.94, 26.35, 27.22, 27.86, 28.05, 34.77, 36.81, 43.49, 48.77, 50.77, 51.19, 101.60, 101.86, 103.89, 110.12, 112.46, 113.55, 120.20, 127.47.

85/15(S)/(R)—(OHF—$Me_2Si$—MCp)Zr($NMe_2$)$_2$. A 100 mL flask with a Teflon inlet valve was charged with Zr($NMe_2$)$_4$ (0.50 g, 1.9 mol) and (OHF—$Me_2Si$—MCp)$H_2$ (0.78 g, 1.8 mmol) in the glove box. Toluene (50 mL) was condensed into the reaction flask in vacuo at −78° C. The reaction mixture was then stirred for 6 h at 120° C. under argon. The solvent was next removed in vacuo, and pentane (20 mL) was transferred in and the mixture filtered. An orange solid (0.90 g, 82 percent yield) was obtained from the filtrate after evaporation.

$^1H$ NMR ($C_6D_6$) δ 0.61 (s, 3H), 0.63 (s, 3H), 0.81 (d, 3H), 0.94 (d, 3H), 1.09 (d, 3H), 1.36 (t, 1H), 1.42–1.89 (m, 14H), 2.24 (d, 1H), 2.26–2.86 (m, 12H), 2.91 (s, 3H), 2.99 (s, 3H), 3.00–3.14 (m, 4H), 5.60 (t, 1H), 5.80 (t, 1H), 6.63 (t, 1H). $^{13}C$ NMR ($C_6D_6$) δ −1.64, −0.28, 15.88, 21.78, 23.00, 23.20, 23.51, 23.62, 24.25, 24.28, 25.41, 26.41, 26.74, 27.55, 33.86, 35.77, 41.40, 42.82, 47.68, 48.86, 51.74, 102.10, 109.13, 110.54, 113.30, 116.41, 119.30, 124.48, 125.21, 132.86, 141.54.

85/15 (S)/(R)—(OHF—$Me_2Si$—MCp)$ZrCl_2$ A 100 mL flask with a Teflon inlet valve was charged with (OHF—$Me_2Si$—MCp)Zr($NMe_2$)$_2$ (0.50 g, 0.82 mmol) in the glove box. The flask was removed from the glove box, and under inert atmosphere, $CH_2Cl_2$ (20 mL) was transferred into the reaction flask at −78° C. Next a solution of $Me_2NH$•HCl (150 mg, 1.80 mmol) l $CH_2Cl_2$ was added dropwise at −78°

C. The resulting clear, yellow solution was stirred at room temperature for 1 h. Removal of solvent under reduced pressure followed by extracting with pentane (50 mL) yielded a pale yellow solid (620 mg, 79 percent yield) after removal of solvent. Two recrystallizations of this solid by slow cooling in pentane yielded a 90/10 (S)/(R) diastereomeric mixture of compounds (20 percent yield). $^1$H NMR δ 0.21 (s, 3H), 0.25 (s, 3H),0.61 (d, 4H), 0.74 (d, 4H), 0.83 (d, 4H), 1.14–1.36 (m, 6H), 1.46 (t, 1H), 1.56–2.06 (m, 6H), 2.0–2.15 (m, 6H), 2.76–3.05 (m, 4H), 5.24 (t, 1H), 5.38 (t, 1H), 6.80 (t, 1H). $^{13}$C NMR ($C_6D_6$) δ −2.16, −1.13, 14.27, 15.89, 21.75, 22.06, 22.29, 22.65, 22.87, 22.96, 25.19, 26.98, 27.29, 27.63, 33.30, 34.40, 35.77, 41.56, 50.83, 96.17, 104.20, 112.08, 114.87, 125.59, 127.19, 130.68, 134.21, 137.28,143.58. Anal. Calcd for $C_{30}H_{44}Cl_2SiZr$: C, 60.57; H. 7.46; N. 0.00. Found: C, 61.09; H. 7.62; N. 0.00.

(R)/(S)—(OHF—$Me_2Si$—MCp)$ZrCl_2$. $Li_2Me_2Si$ ($C_{13}H_{16}$)[(-)-menthylCp] (0.30g, 0 67 mmol) and $ZrCl_4$ (0.16 g, 0.70 mmol) was charged in glove box and $Et_2O$ (20 mL) was condensed in under reduced pressure at −78° C. The mixture was warmed to room temperature and stirred for 30 min. The volatiles were then removed in vacuo, and the residue vacuum dried for 3 h. Pentane (30 mL) was next condensed onto the residue in vacuo, and the solution warmed to ambient temperature. With the aid of an external magnet, the residue was thoroughly mixed and the resulting solution filtered, and the LiCl washed thoroughly with pentane (3×50 mL). The combined extracts were concentrated in vacu, to yield the solid product. $^{13}$C NMR ($C_6D_6$) δ −2.14, −1.95, −1.27, −1.10, 14.26, 15.90, 16.78, 21.77, 22.08, 22.09, 22.32, 22.69, 22.72, 22.89, 22.93, 23.01, 23.05, 25.22, 27.00, 27.22, 27.25, 27.31, 27.41, 27.64, 32.96, 33.31, 34.41, 35.36, 35.80, 40.80, 41.57, 41.61, 43.94, 48.35, 50.86, 96.12, 96.19, 104.21, 105.65, 111.57, 112.09, 114.90, 123.80, 125.61, 127.20, 127.25, 130.56, 130.71, 134.21, 134.47, 136.90, 137.28, 143.59, 148.21.

EXAMPLE 2

Synthesis of 90/10 (S)/(R)—$Me_2Si(Cl_3H_{16})$[(-)-menthylCp]$ZrMe_2$. A 100 mL flask was charged with 90/10 (R)/(S)—$Me_2Si(Cl_3H_{16})$[(-)-menthylCp]$ZrCl_2$ (0.25 g, 0.41 mmol) in the glove box. Toluene (20 mL) was then condensed onto the solid in vacuo at −78° C. MeLi (0.61 ml, 0.85 mmol, 1.4M solution in $Et_2O$) was added dropwise to the solution, and the mixture was stirred 4 h at room temperature. The volatiles were then removed in vacuo, and the residue vacuum dried for 3 h. Pentane (30 mL) was next condensed onto the residue in vacuo, and the solution warmed to ambient temperature. With the aid of an external magnet, the residue was thoroughly mixed, the resulting solution filtered, and the LiCl washed thoroughly with pentane (3×50 mL). The combined extracts were concentrated in vacuo. A white solid product (173 mg, 0.30 mmol) was obtained. $^1$H NMR ($C_6D_6$) δ −0.05 (s, 3H), −0.01 (s, 3H), 0.40 (s, 3H), 0.44 (s, 3H), 0.88 (d, 4H), 1.00 (d, 4H), 1.22 (d, 4H), 1.10–1.35 (m, 4H), 1.37–2.26 (m, 9H), 2.32–2.73 (m, 9H), 2.87 (t, 1H), 5.32 (t, 1H), 5.54 (t, 1H), 6.87 (t, 1H). $^{13}$C NMR ($C_6D_6$) δ −1.97, −0.72, 15.93, 21.89, 22.56, 22.76, 23.03, 23.14, 23.52, 23.67, 25.27, 26.82, 26.98, 27.48, 33.41. 33.79, 34.84, 35.80, 41.31, 41.90, 51.34, 90.14, 98.02, 111.35, 113.09, 119.09, 124.03, 127.39, 127.56, 128.20, 137.52. Anal. Calcd for $C_{32}H_{50}SiZr$; C, 69.30; H. 9.10; N. 0.00. Found C, 69.32; H. 8.87; N. 0.00.

Polymerization

In the glove box, a 100 mL flamed reaction flask equipped with a magnetic stirring bar was charged with metallocene (5–20 mg) and co-catalyst, and the flask then reattached to the high vacuum line. A measured amount of toluene was next condensed onto the solids and the mixture warmed to 0° C. with stirring for 15 min to preactivate the catalyst. The pale yellow to red solution was then equilibrated at the desired reaction temperature using an external constant temperature bath. Gaseous propylene was next introduced with rapid stirring and the pressure maintained at 1 atm by means of a mercury bubbler. After a measured time interval, the reaction was quenched by the addition of acidified methanol. The solvent was removed in vacuo, pentane (50 mL) was then added, and the mixture stirred. The polymer was collected by filtration and washed liberally with pentane followed by methanol. The polymer was then dried in vacuo for several hours. All volatiles were removed from the filtrate and the remaining organics chromatographed on silica with HPLC grade pentane.

Number average(Mn) and weight average (Mw) molecular weights of the resulting polymers were determined by GPC analysis on a Waters 150° C. ALC/GPC; Waters Milennium (version 2.15) chromatography control and data station. The polymer solutions were prepurified by dissolving each sample in hot (T=135° C.) 1,2,4-trichlorobenzene (Aldrich, HPLC grade) and filtered hot through a I gm cellulose filter at 160° C. The $M_n$ and $M_w$ values and the MWD plots were calculated using conventional calibration techniques with polystyrene standards. For the lower molecular weight samples, $M_n$ and $M_w/M_n$ were determined via NMR end-group analysis, GLC, and GC-MS. All measurement were in good agreement. Results are contained in Table 1.

TABLE 1

| Run | Cat. | Cocat. (mole/L) | temp ° C. | $[C_3H_6]^1$ | time (h) | Mn ×10$^3$ | Mw ×10$^3$ | yield (g) | % mmmm |
|---|---|---|---|---|---|---|---|---|---|
| 1 | Ex. 1 | MAO$^2$(180) | 25 | 0.8 | 2.0 | 7.1 | 25.0 | 1.71 | 83 |
|   | "     | "            | 0  | 1.6 | 3.0 | 9.7 | 39.3 | 0.78 | 90 |
| 3 | Ex. 2 | "            | 25 | 0.8 | 2.0 | 6.3 | 18.9 | 5.25 | 85 |
| 4 | "     | TPB$^3$(0.7) | 0  | 1.6 | "   | 5.1 | 13.0 | 0.40 | 90 |
| 5 | "     | CTB$^4$(0.7) | 0  | "   | 0.5 | 24.3 | 70.4 | 1.82 | 89 |

$^1$moles/L
$^2$methylalumoxane
$^3$tris(pentafluorophenyl)borane
$^4$triphenylcarbonium tetrakis(pentafluorophenyl)borate

What is claimed is:

1. A metal complex corresponding to the formula:

wherein:
M independently each occurrence is a metal of Group 4 of the Periodic Table of the Elements;

L₁ is a partially saturated tricyclic group that is bound to M by means of delocalized π-electrons, said group containing up to 50 nonhydrogen atoms and corresponding to the formula:

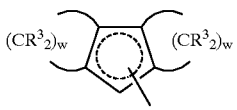

wherein $R^3$ independently each occurrence is hydrogen, or a silyl, hydrocarbyl or silyl-substituted hydrocarbyl group of up to 10 nonhydrogen atoms, and each w, independently, is a whole number from 4 to 6;

L₂ is a substituted cyclopentadienyl group that is bound to M by means of delocalized π-electrons, said cyclopentadienyl group being substituted at one and only one of its two distal positions with a bulky group, $R^4$, selected from the group consisting of $C_{3-20}$ hydrocarbyl groups bonded to the cyclopentadienyl ring by means of a secondary or tertiary substituted carbon atom, and aryl groups of up to 20 carbons, said L₂ group containing up to 50 nonhydrogen atoms;

Z is a divalent substituent bridging L₁ and L₂ of up to 50 non-hydrogen atoms having the formula, $-(ER^2{}_2)_m-$, wherein E independently each occurrence is carbon, silicon or germanium, $R^2$ independently each occurrence is selected from the group consisting of hydrocarbyl, hydrocarbyloxy, silyl, and germyl of up to 20 atoms other than hydrogen, and m is an integer from 1 to 3;

X each occurrence is a monovalent, anionic moiety having up to 40 non-hydrogen atoms, optionally, two X groups may be covalently bound together forming a divalent dianionic moiety having both valences bound to M, further optionally, 2 X groups may be covalently bound together to form a neutral, conjugated or non-conjugated diene that is bonded to M by means of delocalized π-electrons (whereupon M is in the +2 oxidation state), or still further optionally one or more X and one or more X' groups may be bonded together thereby forming a moiety that is both covalently bound to M and coordinated;

m is 1 or 2 and is equal to two less than the formal oxidation state of M, except when 2 X groups together form a neutral conjugated or non-conjugated diene that is π-bonded to M, in which case in is equal to the formal oxidation state of M, X' is a neutral ligand having up to 20 non-hydrogen atoms other than a diene, and optionally X' and L₁ or X' and L₂ are covalently bonded together, and n is a number from 0 to 3.

2. A metal complex according to claim 1 wherein L₁ corresponds to the formula:

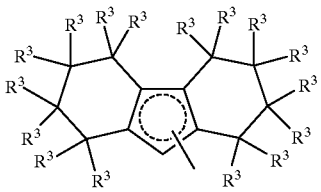

wherein $R^3$ independently each occurrence is hydrogen or $C_{1-6}$ hydrocarbyl.

3. A metal complex according to claim 1 wherein L₁ corresponds to the formula:

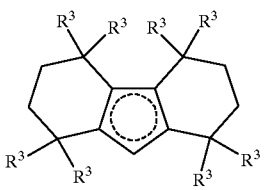

wherein $R^3$ independently each occurrence is hydrogen or $C_{1-4}$ alkyl.

4. A metal complex according to claim 3 wherein L₂ corresponds to the formula:

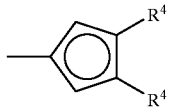

wherein one $R^4$ group is hydrogen and the other $R^4$ group is a $C_{3-20}$ hydrocarbyl group bonded to the cyclopentadienyl ring by means of a secondary or tertiary substituted carbon atom or an aryl group of up to 20 carbons.

5. A catalyst composition comprising an activating cocatalyst and one or more metal complexes according to claim 1.

6. A supported catalyst system comprising a catalyst system according to claim 5 and a substrate.

7. A process for polymerizing propylene, comprising contacting an α-olefin or a mixture of α-olefins comprising propylene with a catalyst composition according to claim 5.

8. A process for polymerizing propylene, comprising contacting an α-olefin or a mixture of α-olefins comprising propylene with a catalyst system according to claim 6.

9. A process according to claim 7 or 8 wherein propylene is homopolymerized.

10. The metal complex any one of claims 1–4 in the form of a solvated adduct, chelated derivative or mixture thereof.

11. The metal complex any one of claims 1–4 in the form of a dimer.

* * * * *

UNITED STATES PATENT AND TRADEMARK OFFICE
CERTIFICATE OF CORRECTION

PATENT NO. : 6,040,401
DATED : March 21, 2000
INVENTOR(S) : Peter N. Nickias et al.

It is certified that error appears in the above-identified patent and that said Letters Patent is hereby corrected as shown below:

Column 1, line 4, insert following heading and paragraph
--<u>Notice of Government Rights</u>
This invention was made with government support under DOE grant No. DE-FG02-86ER13511. The United States Government has certain rights in the invention claimed herein. This invention may be practiced and used by or for the United States Government for governmental purposes, without the payment of any royalties.--

Column 17, claim 1, line 49, "case in is" should correctly read – case m is--.

Signed and Sealed this

Thirteenth Day of February, 2001

*Attest:*

NICHOLAS P. GODICI

*Attesting Officer*  Acting Director of the United States Patent and Trademark Office